US006780810B2

(12) United States Patent
Choudary et al.

(10) Patent No.: US 6,780,810 B2
(45) Date of Patent: Aug. 24, 2004

(54) MULTIFUNCTIONAL CATALYST USEFUL IN THE SYNTHESIS OF CHIRAL VICINAL DIOLS AND PROCESS FOR THE PREPARATION THEREOF, AND PROCESS FOR THE PREPARATION OF CHIRAL VICINAL DIOLS USING SAID MULTIFUNCTIONAL CATALYSTS

(75) Inventors: Boyapati Manoranjan Choudary, Andhra Pradesh (IN); Naidu Sreenivasa Chowdari, Andhra Pradesh (IN); Sateesh Madhi, Andhra Pradesh (IN); Mannepalli Lakshmi Kantam, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 56 days.

(21) Appl. No.: 10/096,072

(22) Filed: Mar. 13, 2002

(65) Prior Publication Data

US 2003/0176746 A1 Sep. 18, 2003

(51) Int. Cl.$^7$ ................................................. B01J 31/00
(52) U.S. Cl. ..................... 502/150; 502/159; 502/163; 502/164; 568/852; 568/860; 568/862; 568/867; 568/811; 525/360; 561/852; 423/599
(58) Field of Search ................. 502/150, 159, 502/163, 164; 568/811, 852, 860, 862, 867; 525/60; 561/852; 423/599

(56) References Cited

U.S. PATENT DOCUMENTS

| 3,156,709 | A | | 11/1964 | Allan | |
|---|---|---|---|---|---|
| 4,390,739 | A | | 6/1983 | Michaelson et al. | |
| 4,544,645 | A | | 10/1985 | Klaassen et al. | |
| 5,093,537 | A | * | 3/1992 | Unruh et al. | 568/862 |
| 5,227,543 | A | * | 7/1993 | Sharpless et al. | 568/860 |
| 5,260,495 | A | * | 11/1993 | Forkner | 568/867 |
| 5,348,725 | A | | 9/1994 | Misra et al. | |
| 5,376,344 | A | | 12/1994 | Chattha et al. | |
| 5,516,929 | A | * | 5/1996 | Sharpless et al. | 560/38 |
| 5,516,967 | A | | 5/1996 | Pandey et al. | |
| 6,124,506 | A | * | 9/2000 | Atkins et al. | 568/618 |
| 6,323,367 | B1 | * | 11/2001 | Choudary et al. | 564/298 |
| 6,387,033 | B1 | * | 5/2002 | Choudary et al. | 568/852 |

FOREIGN PATENT DOCUMENTS

| DE | 906451 | 7/1949 |
|---|---|---|
| EP | 0330224 A1 | 1/1989 |
| EP | 0332380 A3 | 3/1989 |
| EP | 0332380 A2 | 9/1989 |
| EP | 0810192 A1 | 12/1997 |
| FR | 2796312 | 1/2001 |

OTHER PUBLICATIONS

Per Ahlberg, "The Nobel Prize in Chemistry 2001: Catalytic Asymmetric Synthesis", (2001) Royal Swedish Academy of Sciences, 1–12.*

Choudary et al, "Catalytic Asymmetric Dihydroxylation of Olefins With New Catalysts: The First Example of Heterogenization of OSO42– By Ion–Exchange Technique", Journal of the American Chemical Society, American Chemical Society, Washington, D.C., vol. 123, No. 37, 2001, pp. 9220–9221, XP002952604.

* cited by examiner

Primary Examiner—Mark L. Bell
Assistant Examiner—Jennine M. Brown
(74) Attorney, Agent, or Firm—Nixon & Vanderhye, P.C.

(57) ABSTRACT

The present invention relates to a multifunctional reusable catalyst and to a process for the preparation thereof on a single matrix of the support to perform multicomponent reaction in a single pot. The multifunctional catalysts of the invention are useful for the synthesis of chiral vicinal diols by tandem and/or simultaneous reactions involving Heck coupling, N-oxidation and AD reaction of olefins in presence of cinchona alkaloid compounds both as an native one and immobilized one in the said matrix support. This invention also relates to a process for preparing vicinal diols by asymmetric dihydroxylation of olefins in presence of cinchona alkaloid compounds employing reusable multifunctional catalysts as heterogeneous catalysts in place of soluble osmium catalysts.

27 Claims, No Drawings

MULTIFUNCTIONAL CATALYST USEFUL IN THE SYNTHESIS OF CHIRAL VICINAL DIOLS AND PROCESS FOR THE PREPARATION THEREOF, AND PROCESS FOR THE PREPARATION OF CHIRAL VICINAL DIOLS USING SAID MULTIFUNCTIONAL CATALYSTS

FIELD OF THE INVENTION

The present invention relates to a multifunctional reusable catalyst and to a process for the preparation thereof on a single matrix of the support to perform multicomponent reaction in a single pot. More particularly the present invention relates to preparation of multifunctional catalysts consisting of active palladium, tungsten and osmium species useful for the synthesis of chiral vicinal diols by tandem and/or simultaneous reactions involving Heck coupling, N-oxidation and AD reaction of olefins in presence of cinchona alkaloid compounds both as an native one and immobilized one in the said matrix support.

This invention also relates to a process for preparing vicinal diols by asymmetric dihydroxylation of olefins in presence of cinchona alkaloid compounds employing reusable multifunctional catalysts as heterogeneous catalysts in place of soluble osmium catalysts.

BACKGROUND OF THE INVENTION

Products obtained by the dihydroxylation of olefins in presence of cinchona alkaloid compounds are important intermediates for the preparation of drugs and pharmaceuticals. For example the products of cinnamic acid esters are intermediates for taxol side chain. An anticancer drug, diltiazem, calcium antagonist and chloramphenicol can also be derived from the diols obtained through this method.

There are serious disadvantages in performing the catalytic AD reaction with homogeneous system in the manufacture of vicinal diols due to presence of toxic remnants of osmium in products and high cost of osmium tetroxide or potassium osmate dihydrate.

U.S. Pat. Nos. 4,871,855 and 5,260,421 disclose homogeneous asymmetric dihydroxylation of olefins by osmium tetroxide and cinchona alkaloids. The inherent disadvantages in this process are cumbersome procedure for the recovery of the osmium catalyst from the reaction mixture, generation of toxic waste and possibility of presence of toxic osmium in traces in the product.

U.S. Pat. No. 5,516,929 discloses heterogeneous asymmetric dihydroxylation of olefins by osmium tetroxide and polymer-bound cinchona alkaloids. The drawbacks of this process are the difficulty faced in quantitative recovery of toxic osmium catalyst, lower enantioselectivity and reduction in activity and enantioselectivity in each and every recycle experiments.

U.S. Pat. No. 5,968,867 discloses heterogeneous asymmetric dihydroxylation of olefins by osmium tetroxide and silica gel supported bis-cinchona alkaloid derivatives. The drawbacks are difficulty in quantitative recovery of toxic osmium catalyst and reduction in activity and enantioselectivity in each and every recycle experiments.

European patent EP 940,170 A2 discloses catalytic asymmetric dihydroxylation of alkenes using a polymer-supported osmium catalyst. The drawbacks are that higher amount of catalyst (5 mol %), longer reaction time and use of expensive polymer as a support are required.

Reference may be made to a publication J. Am. Chem. Soc. 2001, 123, 1365 wherein asymmetric dihydroxylation of olefins is done by osmium tetroxide and a biomimetic flavin in presence of cinchona alkaloids using $H_2O_2$ as oxidant under homogeneous conditions. The inherent disadvantages are difficulty in the recovery of osmium tetroxide and usage of unstable flavin.

OBJECTS OF THE INVENTION

The main object of the invention is to provide reusable multifunctional catalysts useful for the synthesis of chiral vicinal diols.

Another object of the invention is to prepare reusable multifunctional catalysts having transition metal elements such as palladium, osmium and tugsten deposited in a support having interstitial anions such as chloride, nitrate, carbonate, sulfate or calcined material.

Another object of the invention is to prepare reusable multifunctional catalysts on a single matrix of the support to perform multi-component reaction in a single pot.

It is another object of the invention to provide a novel and ecofriendly process for synthesis of chiral diols from aryl halides and olefins in a single pot.

It is another object of the invention to provide a process for the synthesis of chiral diols dispensing with the use of soluble and toxic osmium tetraoxide or potassium osmate dihydrate.

It is another object of the invention to provide a multifunctional catalysts are prepared and used as heterogeneous catalysts for synthesis of chiral diols which precludes the presence of osmium in traces with product.

It is another object of the invention to provide a process for the synthesis of chiral vicinal diols where enantioselectivity and the yields are good and work-up procedure simple.

It is another object of the invention to provide a process for the synthesis of chiral vicinal diols which is economical and environmentally safe without any disposal problem.

SUMMARY OF THE INVENTION

By employing the heterogeneous catalytic system, the cost naturally comes down due to easy recovery of the catalyst and very insignificant loss of osmium tetroxide, when compared with homogenous system. The products thus obtained using heterogeneous catalyst system are also benign since the presence of osmium in minor impurities in the dihydroxylated products is also precluded.

The present invention provides multifunctional catalysts consisting of palladium, osmium and tungsten species in their composition in its homogeneous or heterogeneous form through ion exchange or anchoring for the preparation of vicinal diols which are important intermediates for drugs and pharmaceuticals.

Accordingly the present invention relates to a reusable multifunctional catalyst useful for the preparation of chiral vicinal diols, the said catalyst having formula S—M, wherein S is a support selected from the group consisting of LDH, resin, silica, clay alumina and S'—$NR_3X$ wherein S' is a unmodified support selected from resin and silica, R is an alkyl group selected from the group consisting of methyl, ethyl, propyl and butyl, X is selected from the group consisting of Cl, Br, I, F, OH and OAc; and M is an active species comprising two or more different transition metals selected from the group consisting of palladium, ruthenium, osmium, tungsten, titanium, vanadium, chromium, manganese, iron, cobalt, nickel, copper, and molybdenum.

In one embodiment of the invention, the active species loading in the catalyst is in the range of 5 to 30% of support.

In another embodiment of the invention, the support as synthesized has an interstitial anion selected from the group consisting of chloride, nitrate, carbonate, sulfate, hydroxide and any mixture thereof.

In another embodiment of the invention, the reusable multifunctional catalyst prepared comprises of LDH-PdOs, resin-PdOs and $SiO_2$—PdOs for the synthesis of chiral diols from aryl halides and olefins and SGS-(QN)$_2$PHAL-PdOs for the preparation of chiral diols from aryl halides and olefins.

In another embodiment of the invention the reusable multifunctional catalyst prepared comprises of LDH-OsW, resin-OsW, $SiO_2$—OsW, SGS-(QN)$_2$PHAL-OsW and SGS-(QN)$_2$PHAL-OsTi for the synthesis of chiral diols from olefins using $H_2O_2$.

In another embodiment of the invention the reusable multifunctional catalyst prepared comprises of LDH-PdOsW, resin-PdOsW, $SiO_2$—PdOsW and SGS-(QN)$_2$PHAL-PdOsW for the preparation of chiral diols from aryl halides and olefins using $H_2O_2$.

The present invention also relates to a process for the preparation of reusable multifunctional catalyst useful for the preparation of chiral vicinal diols, the said catalyst having formula S—M, wherein S is a support selected from the group consisting of LDH, resin, silica, clay alumina and S'—NR$_3$X wherein S' is a unmodified support selected from resin and silica, R is an alkyl group selected from the group consisting of methyl, ethyl, propyl and butyl, X is selected from the group consisting of Cl, Br, I, F, OH and OAc; and M is an active species comprising two or more different transition metals selected from the group consisting of palladium, ruthenium, osmium, tungsten, titanium, vanadium, chromium, manganese, iron, cobalt, nickel, copper, and molybdenum said process comprising reacting salts of two or more said transition metals with said support in an aqueous solvent at a temperature ranging between 20 to 100° C. for a period ranging from 5 to 24 h under nitrogen atmosphere followed by washing to obtain the desired reusable multifunctional catalyst.

In one embodiment of the invention, the active species loading in the catalyst is in the range of 5 to 30% of support.

In another embodiment of the invention, the support as synthesized has an interstitial anion selected from the group consisting of chloride, nitrate, carbonate, sulfate, hydroxide and any mixture thereof In another embodiment of the invention, the reusable multifunctional catalyst prepared is selected from the group consisting of LDH-PdOs, resin-PdOs and $SiO_2$—PdOs for the synthesis of chiral diols from aryl halides and olefins and SGS-(QN)$_2$PHAL-PdOs for the preparation of chiral diols from aryl halides and olefins.

In another embodiment of the invention the reusable multifunctional catalyst prepared is selected from the group consisting of LDH-OsW, resin-OsW, $SiO_2$—OsW, SGS-(QN)$_2$PHAL-OsW and SGS-(QN)$_2$PHAL-OsTi for the synthesis of chiral diols from olefins using $H_2O_2$.

In another embodiment of the invention the reusable multifunctional catalyst prepared is selected from the group consisting of LDH-PdOsW, resin-PdOsW, $SiO_2$—PdOsW and SGS-(QN)$_2$PHAL-PdOsW for the preparation of chiral diols from aryl halides and olefins using $H_2O_2$.

The present invention also relates to a process for the preparation of a chiral vicinal diol from aryl halide and olefin using a reusable multifunctional catalyst having formula S—M, wherein S is a support selected from the group consisting of LDH resin, silica, clay, alumina and S'—NR$_3$X wherein S' is a unmodified support selected from resin and silica, R is an alkyl group selected from the group consisting of methyl, ethyl, propyl and butyl, X is selected from the group consisting of Cl, Br, I, F, OH and OAc; M is an active species comprising two different transition metals at least one of which is palladium and the other is selected from the group consisting of ruthenium, osmium, tungsten, titanium, vanadium, chromium, manganese, iron, cobalt, nickel, copper, and molybdenum, said process comprising reacting aryl halide and olefin using the said catalyst by Heck coupling and asymmetric dihydroxylation in the presence of an oxidant and a cinchona alkaloid compound in a solvent selected from the group consisting of water, acetone, acetonitrile and t-butanol, at a temperature in the range of −20 to 200° C. for a period ranging from 0.5 to 48 hrs and obtaining the desired chiral vicinal diol.

In one embodiment of the invention, the quantity of multifunctional catalyst used in the reaction is in the range of 0.01 to 10 mol % of active species with respect to the substrate.

In one embodiment of the invention, the multifunctional catalyst used is recovered by filtration and is reused for several cycles with consistent activity.

In one embodiment of the invention, the oxidant used is selected from the group consisting of N-methyl morpholine N-oxide (NMO), trimethylamine N-oxide, hydrogen peroxide, t-butyl hydrogen peroxide, potassium ferricyanide, sodium periodate and molecular oxygen.

In one embodiment of the invention, the cinchona alkaloid compound used is selected from the group consisting of (DHQD)$_2$PHAL, (DHQD)$_2$PYR, (DHQD)$_2$AQN, DHQD-OAc, DHQD-CLB, DHQD-PHN, DHQD-MEQ, DHQD-IND and other pseudoenantiomeric forms of such ligands.

The present invention also relates to a process for the preparation of chiral diol from aryl halide and olefin using a reusable multifunctional catalyst having formula S—M, wherein S is a support selected from the group consisting of LDH, resin, silica, clay alumina and S'—NR$_3$X wherein S' is a unmodified support selected from resin and silica, R is an alkyl group selected from the group consisting of methyl, ethyl, propyl and butyl, X is selected from the group consisting of Cl, Br, I, F, OH and OAc; M is an active species comprising three different transition metals at least one of which is palladium and the other two are selected from the group consisting of ruthenium, osmium, tungsten, titanium, vanadium, chromium, manganese, iron, cobalt, nickel, copper, and molybdenum, the said process comprises reacting aryl halide and olefin using the said catalyst by Heck coupling, N-oxidation and asymmetric dihydroxylation in the presence of an oxidant and a cinchona alkaloid compound in a solvent selected from the group consisting of water, acetone, acetonitrile and t-butanol, at a temperature in the range of −20 to 200° C. for a period ranging from 0.5 to 48 hrs and obtaining the desired chiral vicinal diol.

In one embodiment of the invention, the quantity of multifunctional catalyst used in the reaction is in the range of 0.01 to 10 mol % of active species with respect to the substrate.

In one embodiment of the invention, the multifunctional catalyst used is recovered by filtration and is reused for several cycles with consistent activity.

In one embodiment of the invention, the oxidant used is selected from the group consisting of N-methyl morpholine N-oxide (NMO), trimethylamine N-oxide, hydrogen peroxide, t-butyl hydrogen peroxide, potassium ferricyanide, sodium periodate and molecular oxygen.

In one embodiment of the invention, the cinchona alkaloid compound used is selected from the group consisting of $(DHQD)_2PHAL$, $(DHQD)_2PYR$, $(DHQD)_2AQN$, DHQD-OAc, DHQD-CLB, DHQD-PHN, DHQD-MEQ, DHQD-IND and other pseudoenantiomeric forms of such ligands.

In yet another embodiment of the invention, the dihydroxylated chiral vicinal diols are important intermediates for the preparation of drugs and pharmaceuticals, products selected from taxol side chain, an anticancer drug, diltiazem, calcium antagonist and chloramphenicol, an antibiotic.

The present invention also relates to a process for the preparation of chiral diol from olefin using a reusable multifunctional catalyst having formula S—M, wherein S is a support selected from the group consisting of LDH, resin, silica, clay, alumina and S'—$NR_3X$ wherein S' is a unmodified support selected from resin and silica, R is an alkyl group selected from the group consisting of methyl, ethyl, propyl and butyl, X is selected from the group consisting of Cl, Br, I, F, OH and OAc; M is an active species comprising two different transition metals selected from the group consisting of ruthenium, osmium, tungsten, titanium, vanadium, chromium, manganese, iron, cobalt, nickel, copper, and molybdenum, the said process comprises dihydroxylating olefin using the said catalyst via N-oxidation in the presence of an oxidant and a cinchona alkaloid compound in a solvent selected from the group consisting of water, acetone, acetonitrile and t-butanol, at a temperature in the range of −20 to 200° C. for a period ranging from 0.5 to 48 hrs and obtaining the desired chiral vicinal diol.

In one embodiment of the invention, the quantity of multifunctional catalyst used in the reaction is in the range of 0.01 to 10 mol % of active species with respect to the substrate.

In one embodiment of the invention, the multifunctional catalyst used is recovered by filtration and is reused for several cycles with consistent activity.

In one embodiment of the invention, the oxidant used is selected from the group consisting of N-methyl morpholine N-oxide (NMO), trimethylamine N-oxide, hydrogen peroxide, t-butyl hydrogen peroxide, potassium ferricyanide, sodium periodate and molecular oxygen.

In one embodiment of the invention, the cinchona alkaloid compound used is selected from the group consisting of $(DHQD)_2PHAL$, $(DHQD)_2PYR$, $(DHQD)_2AQN$, DHQD-OAc, DHQD-CLB, DHQD-PHN, DHQD-MEQ, DHQD-IND and other pseudoenantiomeric forms of such ligands.

In yet another embodiment of the invention, the dihydroxylated chiral vicinal diols are important intermediates for the preparation of drugs and pharmaceuticals, products selected from taxol side chain, an anticancer drug, diltiazem, calcium antagonist and chloramphenicol, an antibiotic.

DETAILED DESCRIPTION OF THE INVENTION

The novelty in the invention lies in the preparation of multifunctional catalysts through simple exchange process for the first time and use thereof in catalytic amounts for preparing vicinal diols by tandem and/or simultaneous reactions involving Heck coupling, N-oxidation and asymmetric dihydroxylation of olefins employing oxidants in presence of cinchona alkaloid compounds. Higher yields and enantioselectivities are obtained when multifunctional catalysts are used in the synthesis of diols. Since the dihydroxylated products are important intermediates for the preparation of drugs and pharmaceuticals, this invention that envisages reduction of toxic osmium metal content in these products is timely and appropriate. The consistent activity and enantioselectivity obtained for several cycles in multicomponent reaction makes the process economical and possible for commercial realization. Therefore, multifunctional catalysts are better option for the synthesis of vicinal diols. The use of different supports and varied compositions used in the preparation of multifunctional catalysts has no impact on its final form of catalysts with respect to activity and enantioselectivity. Thus this invention offers the best techno-economic route for the synthesis of chiral vicinal diols, intermediates for the preparation of drugs and pharmaceuticals.

Scientific Explanation

In the present invention, multifunctional catalysts have been synthesized for the first time and used in catalytic amounts for preparing vicinal diols by tandem and/or simultaneous reactions involving Heck coupling, N-oxidation and asymmetric dihydroxylation of olefins employing oxidants in presence of cinchona alkaloid compounds in a heterogeneous manner. Multifunctional catalysts are prepared by anion exchange of active species or anchoring through covalent bond formation on various supports originated from inorganic or organic. The metals immobilized on supports are responsible for the multifunctional activity of catalyst. The activity of heterogeneous multifunctional catalysts is similar or higher than the homogeneous counter parts. The higher activity is ascribed to the support effect. Higher yields and enantioselectivities are obtained with multifunctional catalysts used in the multicomponent reaction in aqueous organic solvents. Since the dihydroxylated products are important intermediates for the preparation of drugs and pharmaceuticals, this invention is timely and appropriate. Therefore, multifunctional catalysts are a better option for the synthesis of vicinal diols. The multifunctional catalysts prepared irrespective of support or method of immobilization used in the preparation of multifunctional catalysts offered good yields and enantioselectivies in presence of cinchona alkaloids.

Multifunctional catalysts are prepared and used in catalytic amounts for preparing vicinal diols by multicomponent reaction using oxidants in presence of cinchona alkaloid compounds in a heterogeneous manner are described in the following examples, which are by way of illustration and should not be construed to limit the scope of the invention.

Preparation of Multifunctional Catalysts

EXAMPLE 1

Preparation of LDH-PdOs (I)

1 g of LDH was suspended in 100 mL of aqueous solution containing $Na_2PdCl_4$ and $K_2OsO_4 \cdot 2H_2O$ (0.4 mmol each) and stirred at 25° C. for 12 h under nitrogen atmosphere. The solid catalyst was filtered, washed thoroughly with 500 mL of water and vacuum dried to obtain 1.158 g of LDH-PdOs (0.34 mmol $g^{-1}$ of each Pd and Os).

EXAMPLE 2

Preparation of LDH-OsW (2)

1 g of LDH was suspended in 100 mL of aqueous solution containing $K_2OsO_4 \cdot 2H_2O$ and $Na_2WO_4 \cdot 2H_2O$ (0.4 mmol each) and stirred at 25° C. for 12 h under nitrogen atmosphere. The solid catalyst was filtered, washed thoroughly with 500 mL of water and vacuum dried to obtain 1.172 g of LDH-OsW (0.34 mmol $g^{-1}$ of each Os and W).

EXAMPLE 3
Preparation of LDH-PdOsW (3)

1 g of LDH was suspended in 100 mL of aqueous solution containing $Na_2PdCl_4$, $K_2OsO_4.2H_2O$ and $Na_2WO_4.2H_2O$ (0.3 mmol each) and stirred at 25° C. for 12 h under nitrogen atmosphere. The solid catalyst was filtered, washed thoroughly with 500 mL of water and vacuum dried to obtain 1.181 g of LDH-PdOsW (0.25 mmol $g^{-1}$ of each Pd, Os and W).

EXAMPLE 4
Preparation of resin-PdOsW (4)

Resin was obtained by quaternization of triethylamine (2.1 mL, 21 mmol) with 1 g of chloromethylated styrene-divinylbenzene copolymer (Merrifield resin, capacity ~2.1 mequiv/g) in chloroform (20 mL) under reflux for 24 h. 1 g of quaternary ammonium resin was suspended in 100 mL of aqueous solution containing $Na_2PdCl_4$, $K_2OsO_4.2H_2O$ and $Na_2WO_4.2H_2O$ (0.25 mmol each) and stirred at 25° C. for 12 h under nitrogen atmosphere. The solid catalyst was filtered, washed thoroughly with 500 mL of water and vacuum dried to obtain resin-PdOsW (0.2 mmol $g^{-1}$ of each Pd, Os and W).

EXAMPLE 5
Preparation of $SiO_2$—PdOsW (5)

Modified silica was obtained by quaternisation of triethylamine (0.7 mL, 7 mmol) with bromopropylsilica (capacity 0.7 mequiv/g) in chloroform (20 mL) under reflux for 24 h. 1 g of quaternary ammonium silica was suspended in 100 mL of aqueous solution containing $Na_2PdCl_4$, $K_2OsO_4.2H_2O$ and $Na_2WO_4.2H_2O$ (0.11 mmol each) and stirred at 25° C. for 12 h under nitrogen atmosphere. The solid catalyst was filtered, washed thoroughly with 500 mL of water and vacuum dried to obtain $SiO_2$—PdOsW (0.1 mmol $g^1$ of each Pd, Os and W).

EXAMPLE 6
Preparation of SGS-(QN)$_2$PHAL-OsTi (6)

Silica gel (200 mesh) (4 g) was treated with 18 ml of 3-mercaptopropyl trimethoxysilane in 22 ml of anhydrous 1:1 pyridine/toluene. The slurry was heated at 90° C. for 24 h. After filtration, the solid was washed with toluene followed by soxhlet extraction with toluene and dried under vacuum for 1 h to give 3-mercaptopropyl silica gel containing 3.38% S, corresponding to 1.05 mmol of S per gram. This derivatised silica gel (2 g) was suspended in chloroform and refluxed with 4-(9-O-dihydroquinyl)-1-(9-O-quinyl) phathalazine (0.781 g) and AIBN (55 mg) as radical initiator for 48 h. The solid was filtered followed by washing with methanol, soxhlet extraction with toluene and drying under vacuum for 1 h to give SGS-(QN)$_2$PHAL (15 wt. % of N, corresponding to 0.2 mmol of alkaloid per gram). To this $OsO_4$ and TS-1(0.038 mmol/g, Si/Ti: 32), each 1 equivalent in acetonitrile was stirred for 30 min and solvent was evaporated to get SGS-(QN)$_2$PHAL-OsTi.

EXAMPLE 7
Preparation of SGS-(QN)$_2$PHAL-PdOs (7)

2 g of SGS-(QN)$_2$PHAL was treated with $PdCl_2$ (2 mmol) in acetone (10 mL) under reflux for 24 h. The dark yellow powder was filtered, washed with acetone, then stirred with hydrazine hydrate (1.5 mL) and ethanol (10 mL) at room temperature for 4 h. The resulting solid was filtered, washed with ethanol and dried under vacuum for 1 h to give a light green colored solid, SGS-(QN)$_2$PHAL-Pd (0.2 mmol of palladium per gram), subsequent complexation with $OsO_4$ (0.2 mmol per gram) obtained SGS-(QN)$_2$PHAL-PdOs.

EXAMPLE 8
Preparation of SGS-(QN)$_2$PHAL-PdOsW (8)

SGS-(QN)$_2$PHAL-PdOs as synthesized in example 7 was mixed with 1 equivalent of tungstate exchanged quaternary ammonium form of silica to obtain SGS-(QN)$_2$PHAL-PdOsW.

Synthesis of Chiral Diols

The synthesis of chiral diols was performed using the following methods in order to evaluate multifunctional catalysts s of the present invention.

EXAMPLE 9
Synthesis of (R,R)-(+)-1,2-diphenyl-1,2-ethanediol using LDH-PdOs 1 mol % of LDH-PdOs, 1 mM iodobenzene, 1 mM styrene and 1.1 mM $Et_3N$ were stirred at 70° C. for 8 h. At this stage, the heating was stopped and a mixture of (DHQD)$_2$PHAL (1 mol %) and 1.3 mM NMO in 5 ml of $^t$butanol-water (5:1) was added and stirred at room temperature. After completion of the diol formation (4–6 h, as monitored by TLC), the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 10
Synthesis of (R,R)-(+)-1,2-diphenyl-1,2-ethanediol using LDH-OsW

LDH-OsW (0.01 mmol), NMM(0.5 mmol), (DHQD)$_2$PHAL(0.03 mmol, 23 mg) and ⅕ of the $H_2O_2$ (⅕×1.5 mmol) were taken in a round bottomed flask containing $^t$BuOH-water (3:1, 5 mL) and stirred at room temperature for 20 min. To this mixture was added an olefin (1 mmol) and the rest of the $H_2O_2$ over a period of 10 h using separate syringe pumps. After the addition was complete the reaction mixture was stirred for another 2 h and filtered, washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 11
Synthesis of (R,R)-(+)-1,2-diphenyl-1,2-ethanediol using LDH-PdOsW 1 mol % of LDH-PdOsW, 1 mM iodobenzene, 1 mM styrene and 1.1 mM $Et_3N$ were stirred at 70° C. for 8 h. After completion of Heck coupling as monitored by TLC, the heating was stopped and a mixture of (DHQD)$_2$PHAL (1 mol %) and 0.5 mM of NMM in 5 ml of $^t$butanol-water (5:1) was added in one portion to the reaction flask. 1.5 mM of $H_2O_2$ was then slowly added over a period of 12 h. After the addition was complete, the resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol. The recovered catalyst was reused with consistent activity for four runs (examples 28–32).

EXAMPLE 12
Synthesis of (R,R)-(+)-1,2-diphenyl-1,2-ethanediol using resin-PdOsW 1 mol % of resin-PdOsW, 1 mM iodobenzene, 1 mM styrene and 1.1 mM $Et_3N$ were stirred at 70° C. for 8 h. After completion of Heck coupling as monitored by TLC, the heating was stopped and a mixture of (DHQD)$_2$PHAL (1 mol %) and 0.5 mM of NMM in 5 ml of $^t$butanol-water (5:1) was added in one portion to the reaction flask. 1.5 mM of H$_2$O$_2$ was then slowly added over a period of 12 h. After the addition was complete, the resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to get the corresponding cis-diol.

EXAMPLE 13

Synthesis of (R,R)-(+)-1,2-diphenyl-1,2-ethanediol using SiO$_2$—PdOsW 1 mol % of SiO$_2$—PdOsW, 1 mM iodobenzene, 1 mM styrene and 1.1 mM Et$_3$N were stirred at 70° C. for 8 h. After completion of Heck coupling as monitored by TLC, the heating was stopped and a mixture of (DHQD)$_2$PHAL (1 mol %) and 0.5 mM of NMM in 5 ml of $^t$butanol-water (5:1) was added in one portion to the reaction flask. 1.5 mM of H$_2$O$_2$ was then slowly added over a period of 12 h. After the addition was complete, the resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 14

Synthesis of (R,R)-(+)-1,2-diphenyl-1,2-ethanediol using SGS-(QN)$_2$PHAL-OsTi system by H$_2$O$_2$ oxidant.

SGS-(QN)$_2$PHAL-OsTi (0.01 mmol), NMM(0.25 mmol), TEAA(2 mmol) and ⅓ of the H$_2$O$_2$ (⅓×1.5 mmol) were taken in a round-bottomed flask containing $^t$BuOH-water (3:1, 5 mL) and stirred at room temperature for 20 min. To this mixture was added an olefin (1 mmol) and the rest of the H$_2$O$_2$ over a period of 12 h using separate syringe pumps. After the addition was complete the reaction mixture was stirred for another 2 h and the catalyst was filtered and washed with ethyl acetate. The solvent was removed and the crude material was chromatographed on silica gel to afford the corresponding cis-diol.

EXAMPLE 15

Synthesis of (R,R)-(+)-1,2-diphenyl-1,2-ethanediol using SGS-(QN)$_2$PHAL-PdOs by NMO oxidant.

Catalyst 7 (100 mg, 0.02 mmol), 1 mM iodobenzene, 1 mM styrene and 1.1 mM Et$_3$N in acetonitrile (5 ml) were stirred at 70° C. for 8 h. At this stage, the heating was stopped and solvent was removed under vacuum. 1.3 mM of NMO in 5 ml of $^t$butanol-water (3:1) was added and stirred at room temperature for 12 h. After completion of the reaction, the catalyst was filtered and washed with ethyl acetate. After removing the solvent, the crude material was chromatographed on silica gel to afford the corresponding cis-diol.

EXAMPLE 16

Synthesis of (R,R)-(+)-1,2-diphenyl-1,2-ethanediol using SGS-(QN)$_2$PHAL-PdOs by K$_3$Fe(CN)$_6$ oxidant.

Catalyst (100 mg, 0.02 mmol), 1 mM iodobenzene, 1 mM styrene and 4 mM K$_2$CO$_3$ in acetonitrile (5 ml) were stirred at 70° C. for 8 h. At this stage, the heating was stopped and solvent was removed under vacuum. 3 mM of K$_3$(FeCN)$_6$ in 10 ml of $^t$butanol-water (1:1) was added and stirred at room temperature for 12 h. After completion of the reaction, the catalyst was filtered and washed with ethyl acetate. After removing the solvent, the crude material was chromatographed on silica gel to afford the corresponding cis-diol.

EXAMPLE 17

Synthesis of (R,R)-(+)-1,2-diphenyl-1,2-ethanediol using Na$_2$PdCl$_4$/K$_2$OsO$_4$.2H$_2$O by NMO oxidant.

Na$_2$PdCl$_4$ (1 mol %), K$_2$OsO$_4$.2H$_2$O (1 mol %), 1 mM iodobenzene, 1 mM styrene and 1.1 mM Et$_3$N were stirred at 70° C. for 8 h. At this stage, the heating was stopped and a mixture of (DHQD)$_2$PHAL (1 mol %) and 1.3 mM NMO in 5 ml of $^t$butanol-water (5:1) was added and stirred at room temperature. After completion of the diol formation (4–6 h, as monitored by TLC), toluene was added to the reaction mixture to get the phase separation and the aqueous phase was extracted with toluene (2×5 mL). The organic phase was washed with 1N HCl to recover the chiral ligand. The organic solvent was removed and the crude material was chromatographed on silica gel to afford the corresponding cis-diol.

EXAMPLE 18

Synthesis of (R,R)-(+)-1,2-diphenyl-1,2-ethanediol using K$_2$OsO$_4$.2H$_2$O/Na$_2$WO$_4$.2H$_2$O K$_2$OsO$_4$.2H$_2$O (3.68 mg, 0.01 mmol), Na$_2$WO$_4$.2H$_2$O (3.29 mg, 0.01 mmol), NMM(0.5 mmol), (DHQD)$_2$PHAL (0.03 mmol, 23 mg) and ⅓ of the H$_2$O$_2$ (⅓×1.5 mmol) were taken in a round bottomed flask containing $^t$BuOH-water (3:1, 5 mL) and stirred at room temperature for 20 min. To this mixture was added an olefin (1 mmol) and the rest of the H$_2$O$_2$ over a period of 10 h using separate syringe pumps. After the addition was complete the reaction mixture was stirred for another 2 h. Toluene was added to the reaction mixture to get the phase separation and the aqueous phase was extracted with toluene (2×5 mL). The organic phase was washed with 1N HCl to recover the chiral ligand. The organic solvent was removed and the crude material was chromatographed on silica gel to afford the corresponding cis-diol.

EXAMPLE 19

Synthesis of (R,R)-(+)-1,2-diphenyl-1,2-ethanediol using Na$_2$PdCl$_4$/K$_2$OsO$_4$.2H$_2$O/Na$_2$WO$_4$.2H$_2$O Na$_2$PdCl$_4$ (2.94 mg, 0.01 mmol), K$_2$OsO$_4$.2H$_2$O (3.68 mg, 0.01 mmol), Na$_2$WO$_4$.2H$_2$O (3.29 mg, 0.01 mmol), 1 mM iodobenzene, 1 mM styrene and 1.1 mM Et$_3$N were stirred at 70° C. for 8 h. After completion of Heck coupling as monitored by TLC, the heating was stopped and a mixture of (DHQD)$_2$PHAL (3 mol %) and 0.5 mM of NMM in 5 ml of $^t$butanol-water (5:1) was added in one portion to the reaction flask. 1.5 mM of H$_2$O$_2$ was then slowly added over a period of 12 h. After the addition was complete, the resulting solution was stirred for an additional 1 h. Toluene was added to the reaction mixture to get the phase separation and the aqueous phase was extracted with toluene (2×5 mL). The organic phase was washed with 1N HCl to recover the chiral ligand. The organic solvent was removed and the crude material was chromatographed on silica gel to afford the corresponding cis-diol. The metal salts can be recovered and reused for the next reaction by evaporation of the aqueous phase.

LDH-PdOsW Catalyzed Synthesis of Chiral Diols

EXAMPLE 20

Synthesis of (R,R)-(+)-1,2-diphenyl-1,2-ethanediol 1 mol % of LDH-PdOsW, 1 mM bromobenzene, 1 mM styrene and 1.1 mM Et$_3$N were stirred at 70° C. for 16 h.

After completion of the Heck coupling as monitored by TLC, the heating was stopped and a mixture of (DHQD)$_2$ PHAL (1 mol %) and 0.5 mM of NMM in 5 ml of $^t$butanol-water (5:1) was added in one portion to the reaction flask. 1.5 mM of H$_2$O$_2$ was then slowly added over a period of 12 h. After the addition was complete, the resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 21
Synthesis of (R,R)-(+)-1-(4-methoxyphenyl),2-phenylethanediol 1 mol % of LDH-PdOsW, 1 mM 4-iodoanisole, 1 mM styrene and 1.1 mM Et$_3$N were stirred at 70° C. for 8 h. After completion of Heck coupling as monitored by TLC, the heating was stopped and a mixture of (DHQD)$_2$PHAL (1 mol %) and 0.5 mM of NMM in 5 ml of $^t$butanol-water (5:1) was added in one portion to the reaction flask. 1.5 mM of H$_2$O$_2$ was then slowly added over a period of 12 h. After the addition was complete, the resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 22
Synthesis of (R,R)-(+)-1-(4-methylphenyl),2-phenylethanediol 1 mol % of LDH-PdOsW, 1 mM 4-iodotoluene, 1 mM styrene and 1.1 mM Et$_3$N were stirred at 70° C. for 8 h. After completion of Heck coupling as monitored by TLC, the heating was stopped and a mixture of (DHQD)$_2$PHAL (1 mol %) and 0.5 mM of NMM in 5 ml of $^t$butanol-water (5:1) was added in one portion to the reaction flask. 1.5 mM of H$_2$O$_2$ was then slowly added over a period of 12 h. After the addition was complete, the resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 23
Synthesis of (R,R)-(+)-1-(4-chlorophenyl),2-phenylethanediol 1 mol % of LDH-PdOsW, 1 mM 4-chloroiodobenzene, 1 mM styrene and 1.1 mM Et$_3$N were stirred at 70° C. for 8 h. After completion of Heck coupling as monitored by TLC, the heating was stopped and a mixture of (DHQD)$_2$PHAL (1 mol %) and 0.5 mM of NMM in 5 ml of $^t$butanol-water (5:1) was added in one portion to the reaction flask. 1.5 mM of H$_2$O$_2$ was then slowly added over a period of 12 h. After the addition was complete, the resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 24
Synthesis of (R,R)-(+)-4,4'-Dimethyldiphenyl-1,2-ethanediol 1 mol % of LDH-PdOsW, 1 mM 4-iodotoluene, 1 mM 4-methylstyrene and 1.1 mM Et$_3$N were stirred at 70° C. for 16 h. After completion of Heck coupling as monitored by TLC, heating was stopped and a mixture of (DHQD)$_2$PHAL (1 mol %) and 0.5 mM of NMM in 5 ml of $^t$butanol-water (5:1) was added in one portion to the reaction flask. 1.5 mM of H$_2$O$_2$ was then slowly added over a period of 12 h. After the addition was complete, resulting solution was stirred for an additional 1 h and the catalyst was filtered and washed with ethyl acetate. Combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 25
Synthesis of (R,R)-(+)-4,4'-Dimethoxydiphenyl-1,2-ethanediol 1 mol % of LDH-PdOsW, 1 mM 4-iodoanisole, 1 mM 4-methoxystyrene and 1.1 mM Et$_3$N were stirred at 70° C. for 16 h. After completion of Heck coupling as monitored by TLC, the heating was stopped and a mixture of (DHQD)$_2$ PHAL (1 mol %) and 0.5 mM of NMM in 5 ml of $^t$butanol-water (5:1) was added in one portion to reaction flask. 1.5 mM of H$_2$O$_2$ was then slowly added over a period of 12 h. After the addition was complete, resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 26
Synthesis of (2S,3R)-(−)-Methyl-2,3-dihydroxy-3-phenylpropionate 1 mol % of LDH-PdOsW, 1 mM iodobenzene, 1 mM methyl acrylate and 1.1 mM Et$_3$N were stirred at 70° C. for 8 h. After completion of Heck coupling as monitored by TLC, the heating was stopped and a mixture of (DHQD)$_2$ PHAL (1 mol %) and 0.5 mM of NMM in 5 ml of $^t$butanol-water (5:1) was added in one portion to reaction flask. 1.5 mM of H$_2$O$_2$ was then slowly added over a period of 12 h. After the addition was complete, resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 27
Synthesis of (2S,3R)-(−)-Ethyl-2,3-dihydroxy-3-(4-methoxyphenyl)propionate 1 mol % of LDH-PdOsW, 1 mM iodoanisole, 1 mM ethyl acrylate and 1.1 mM Et$_3$N were stirred at 70° C. for 8 h. After completion of Heck coupling as monitored by TLC, heating was stopped and a mixture of (DHQD)$_2$PHAL (1 mol %) and 0.5 mM of NMM in 5 ml of $^t$butanol-water (5:1) was added in one portion to reaction flask. 1.5 mM of H$_2$O$_2$ was then slowly added over a period of 12 h. After the addition was complete, resulting solution was stirred for an additional 1 h and the catalyst was filtered and washed with ethyl acetate. The combined filtrates were extracted with 1N HCl (2×5 mL) to recover the chiral ligand from the aqueous layer. After removing the solvent, the crude material was chromatographed on silica gel using hexane/ethyl acetate as an eluant to afford the corresponding cis-diol.

EXAMPLE 28

Synthesis of (R,R)-(+)-1,2-diphenyl-1,2-ethanediol using SGS-(QN)$_2$PHAL-PdOsW 1 mol % of SGS-(QN)$_2$PHAL-PdOsW, 1 mM iodobenzene, 1 mM styrene and 1.1 mM Et$_3$N in acetonitrile (5 ml) were stirred at 70° C. for 8 h. At this stage, heating was stopped and solvent was removed under vacuum. To this 0.5 mM of NMM in 5 ml of $^t$butanol-water (5:1) was added in one portion to reaction flask. 1.5 mM of H$_2$O$_2$ was then slowly added over a period of 12 h. After the addition was complete, resulting solution was stirred for an additional 1 h and the catalyst was filtered and washed with ethyl acetate. After removing the solvent, the crude material was chromatographed on silica gel using hexane/ethyl acetate as an eluant to afford the corresponding cis-diol.

Reuse of LDH-PdOsW in the Synthesis of (R,R)-(+)-1,2-diphenyl-1,2-ethanediol

EXAMPLE 29

Synthesis of (R,R)-(+)-1,2-diphenyl-1,2-ethanediol using LDH-PdOsW, which is recovered from Example 10.

The reaction was performed using an identical process as in example 5 (yield 84%, ee 99%).

EXAMPLE 30

Synthesis of (R,R)-(+)-1,2-diphenyl-1,2-ethanediol using LDH-PdOsW, which is recovered from Example 29.

The reaction was performed using an identical process as in example 10 (yield 86%, ee 99%).

EXAMPLE 31

Synthesis of (R,R)-(+)-1,2-diphenyl-1,2-ethanediol using LDH-PdOsW, which is recovered from Example 30.

The reaction was performed using an identical process as in example 10 (yield 84%, ee 99%).

EXAMPLE 32

Synthesis of (R,R)-(+)-1,2-diphenyl-1,2-ethanediol using LDH-PdOsW, which is recovered from Example 31.

The reaction was performed using an identical process as in example 10 (yield 85%, ee 99%).

The experimental results in the Examples 9 to 32 are provided in Tables 1–3.

TABLE 1

Synthesis of (R,R)-(+)-1,2-diphenyl-1,2-ethanediol with various multifunctional catalysts.

| Example | catalyst | Aryl halide | olefin | oxidant | Diol Yield | ee |
|---|---|---|---|---|---|---|
| 9 | 1 | iodobenzene | styrene | NMO | 91 | 99 |
| 10 | 2 | | stilbene | H$_2$O$_2$ | 93 | 99 |
| 11 | 3 | iodobenzene | styrene | H$_2$O$_2$ | 85 | 99 |
| 12 | 4 | iodobenzene | styrene | H$_2$O$_2$ | 83 | 99 |
| 13 | 5 | iodobenzene | styrene | H$_2$O$_2$ | 82 | 99 |
| 14 | 6 | | stilbene | H$_2$O$_2$ | 75 | 99 |
| 15 | 7 | Iodobenzene | styrene | NMO | 90 | 99 |
| 16 | 7 | iodobenzene | styrene | K$_3$Fe(CN)$_6$ | 92 | 99 |
| 17 | 8 | iodobenzene | styrene | H$_2$O$_2$ | 83 | 99 |
| 18 | Na$_2$PdCl$_4$/K$_2$OsO$_4$ | iodobenzene | styrene | NMO | 90 | 99 |
| 19 | K$_2$OsO$_4$/Na$_2$WO$_4$ | | stilbene | H$_2$O$_2$ | 91 | 99 |
| 20 | Na$_2$PdCl$_4$/K$_2$OsO$_4$/Na$_2$WO$_4$ | iodobenzene | styrene | H$_2$O$_2$ | 82 | 99 |

TABLE 2

LDH-PdOsW catalyzed synthesis of chiral diols using (DHQD)$_2$PHAL as a chiral ligand.

| Example | Aryl halide | olefin | product | Yield[a] | ee[b] |
|---|---|---|---|---|---|
| 21 | bromobenzene | styrene | 1,2-diphenyl-1,2-ethanediol | 86 | 99 |
| 22 | 4-iodoanisole | styrene | 1-(4-methoxyphenyl),2-phenylethanediol | 85 | 99 |
| 23 | 4-iodotoluene | styrene | 1-(4-methylphenyl),2-phenylethanediol | 91 | 99 |
| 24 | 4-chloroiodobenzene | styrene | 1-(4-chlorophenyl),2-phenylethanediol | 89 | 97 |
| 25 | 3-iodotoluene | 4-methylstyrene | 4,4'-Dimethyldiphenyl-1,2-ethanediol | 86 | 99 |
| 26 | 4-iodoanisole | 4-methylanisole | 4,4'-Dimethoxydiphenyl-1,2-ethanediol | 83 | 99 |
| 27 | iodobenzene | Methyl acrylate | Methyl-2,3-dihydroxy-3-phenylpropionate | 90 | 98 |
| 28 | 4-iodoanisole | Ethyl acrylate | Ethyl-2,3-dihydroxy-3-(4-methoxyphenyl)propionate | 93 | 96 |

[a]Yield percent after the separation by using column chromatography.
[b]% e.e.(e.e. means enantiomeic excess) was determined by chiral HPLC analysis

TABLE 3

Reuse of LDH-PdOsW in the synthesis of (R,R)-(+)-1,2-diphenyl-1,2-ethanediol

| Ex. No | run | yield | ee |
|---|---|---|---|
| 11 | 1 | 85 | 99 |
| 29 | 2 | 84 | 99 |
| 30 | 3 | 86 | 99 |
| 31 | 4 | 84 | 99 |
| 32 | 5 | 85 | 99 |

The Main Advantages of the Present Invention are:
1. The process for the synthesis of chiral diols from aryl halides and olefins in a single pot is novel and ecofriendly. The present process dispenses with the use of soluble, toxic osmium tetraoxide or potassium osmate dihydrate and instead uses novel heterogeneous reusable multifunctional catalysts. The catalyst of the invention is important since it can catalyse three different reactions by generating the precursors, pro chiral olefins and NMO for AD reaction in situ from the readily available cheaper starting materials such as styrenes and aryl halides thereby saving energy and time vital for a better and economical process. The catalysts used are economical and do not present a problem of disposal.
2. Multifunctional recyclable catalysts are used as heterogeneous catalysts for synthesis of chiral diols, thereby precluding the presence of osmium in traces with product
3. The enantioselectivity and the yields are good and the work-up procedure is simple.

We claim:

1. A reusable multifunctional catalyst useful for the preparation of chiral vicinal diols, the said catalyst having formula S—M, wherein S is a support selected from the group consisting of LDH, resin, silica, clay alumina and S'—NR$_3$X wherein S' is a unmodified support selected from resin and silica, R is an alkyl group selected from the group consisting of methyl, ethyl, propyl and butyl, X is selected from the group consisting of Cl, Br, I, F, OH and OAc; and M is an active species comprising two or more different transition metals selected from the group consisting of palladium, ruthenium, osmium, tungsten, titanium, vanadium, chromium, manganese, iron, cobalt, nickel, copper, and molybdenum, and wherein the reusable multifunctional catalyst is selected from the group consisting of LDH-PdOs, resin-PdOs SiO$_2$—PdOs, SGS-(QN)$_2$PHAL-PdOs, LDH-OsW, resin-OsW, SiO$_2$—OsW, SGS-(QN)$_2$PHAL-OsW, SGS-(QN)$_2$PHAL-OsTi, LDH-PdOsW, resin-PdOsW, SiO$_2$—PdOsW and SGS-(QN)$_2$PHAL-PdOsW.

2. A catalyst as claimed in claim 1 wherein the active species loading in the catalyst is in the weight range of 5 to 30% of the support.

3. A catalyst as claimed in claim 1 wherein the support as synthesized has an interstitial anion selected from the group consisting of chloride, nitrate, carbonate, sulfate, hydroxide and any mixture thereof.

4. A catalyst as claimed in claim 1 wherein the reusable multifunctional catalyst is selected from the group consisting of LDH-PdOs, resin-PdOs and SiO$_2$—PdOs for the synthesis of chiral diols from aryl halides and olefins and SGS-(QN)$_2$PHAL-PdOs for the preparation of chiral diols from aryl halides and olefins.

5. A catalyst as claimed in claim 1 wherein the reusable multifunctional catalyst prepared is selected from the group consisting of LDH-OsW, resin-OsW, SiO$_2$—OsW, SGS-(QN)$_2$PHAL-OsW and SGS-(QN)$_2$PHAL-OsTi for the synthesis of chiral diols from olefins using H$_2$O$_2$.

6. A catalyst as claimed in claim 1 wherein the reusable multifunctional catalyst prepared is selected from the group consisting of LDH-PdOsW, resin-PdOsW, SiO$_2$—PdOsW and SGS-(QN)$_2$PHAL-PdOsW for the preparation of chiral diols from aryl halides and olefins using H$_2$O$_2$.

7. A process for the preparation of reusable multifunctional catalyst useful for the preparation of chiral vicinal diols, the said catalyst having formula S—M, wherein S is a support selected from the group consisting of LDH, resin, silica, clay alumina and S'—NR$_3$X wherein S' is a unmodified support selected from resin and silica, R is an alkyl group selected from the group consisting of methyl, ethyl, propyl and butyl, X is selected from the group consisting of Cl, Br, I, F, OH and OAc; and M is an active species comprising two or more different transition metals selected from the group consisting of palladium, ruthenium, osmium, tungsten, titanium, vanadium, chromium, manganese, iron, cobalt, nickel, copper, and molybdenum said process comprising reacting salts of two or more said transition metals with said support in an aqueous solvent at a temperature ranging between 20 to 100° C. for a period ranging from 5 to 24 h under nitrogen atmosphere followed by washing to obtain the desired reusable multifunctional catalyst, and wherein the reusable multifunctional catalyst is selected from the group consisting of LDH-PdOs, resin-PdOs, SiO$_2$—PdOs, SGS-(QN)$_2$PHAL-PdOs, LDH-OsW, resin-OsW, SiO$_2$OsW, SGS-(QN)$_2$PHAL-OsW, SGS-(QN)$_2$PHAL-OsTi, LDH-PdOsW, resin-PdOsW, SiO$_2$—PdOsW and SGS-(QN)$_2$PHAL-PdOsW.

8. A process as claimed in claim 7 wherein the active species loading in the catalyst is in the weight range of 5 to 30% of the support.

9. A process as claimed in claim 7 wherein the support as synthesized has an interstitial anion selected from the group consisting of chloride, nitrate, carbonate, sulfate, hydroxide and any mixture thereof.

10. A process as claimed in claim 7 wherein the reusable multifunctional catalyst prepared comprises LDH-PdOs, resin-PdOs and SiO$_2$—PdOs for the synthesis of chiral diols from aryl halides and olefins and SGS-(QN)$_2$PHAL-PdOs for the preparation of chiral diols from aryl halides and olefins.

11. A process as claimed in claim 7 wherein the reusable multifunctional catalyst prepared comprises LDH-OsW, resin-OsW, SiO$_2$—OsW, SGS-(QN)$_2$PHAL-OsW and SGS-(QN)$_2$PHAL-OsTi for the synthesis of chiral diols from olefins using H$_2$O$_2$.

12. A process as claimed in claim 7 wherein the reusable multifunctional catalyst prepared comprises LDH-PdOsW, resin-PdOsW, SiO$_2$—PdOsW and SGS-(QN)$_2$PHAL-PdOsw for the preparation of chiral diols from aryl halides and olefins using H$_2$O$_2$.

13. A process for the preparation of a chiral vicinal diol from aryl halide and olefin using a reusable multifunctional catalyst having formula S—M, wherein S is a support selected from the group consisting of LDH, resin, silica, clay, alumina and S'—NR$_3$X wherein S' is a unmodified support selected from resin and silica, R is an alkyl group selected from the group consisting of methyl, ethyl, propyl and butyl, X is selected from the group consisting of Cl, Br, I, F, OH and OAc; M is an active species comprising two different transition metals at least one of which is palladium and the other is selected from the group consisting of ruthenium, osmium, tungsten, titanium, vanadium, chromium, manganese, iron, cobalt, nickel, copper, and molybdenum, said process comprising reacting aryl halide and olefin using the said catalyst by Heck coupling and asymmetric dihydroxylation in the presence of an oxidant and a cinchona alkaloid compound in a solvent selected from the group consisting of water, acetone, acetonitrile and t-butanol, at a temperature in the range of −20 to 200° C. for a period ranging from 0.5 to 48 hrs and obtaining the desired chiral vicinal diol.

14. A process as claimed in claim 13 wherein the quantity of multifunctional catalyst used in the reaction is in the range of 0.01 to 10 mol % of active species with respect to the substrate.

15. A process as claimed in claim 13 wherein the multifunctional catalyst used is recovered by filtration and is reused for several cycles with consistent activity.

16. A process as claimed in claim 13 wherein the oxidant used is selected from the group consisting of N-methyl morpholine N-oxide (NMO), trimethylamine N-oxide, hydrogen peroxide, t-butyl hydrogen peroxide, potassium ferricyanide, sodium periodate and molecular oxygen.

17. A process as claimed in claim 13 wherein the cinchona alkaloid compound used is selected from the group consisting of $(DHQD)_2PHAL$, $(DHQD)_2PYR$, $(DHQD)_2AQN$, DHQD-OAc, DHQD-CLB, DHQD-PHN, DHQD-MEQ, DHQD-IND and other pseudoenantiomeric forms of such ligands.

18. A process for the preparation of chiral diol from aryl halide and olefin using a reusable multifunctional catalyst having formula S—M, wherein S is a support selected from the group consisting of LDH, resin, silica, clay alumina and S'—$NR_3X$ wherein S' is a unmodified support selected from resin and silica, R is an alkyl group selected from the group consisting of methyl, ethyl, propyl and butyl, X is selected from the group consisting of Cl, Br, I, F, OH and OAc; M is an active species comprising three different transition metals at least one of which is palladium and the other two are selected from the group consisting of ruthenium, osmium, tungsten, titanium, vanadium, chromium, manganese, iron, cobalt, nickel, copper, and molybdenum, the said process comprises reacting aryl halide and olefin using the said catalyst by Heck coupling, N-oxidation and asymmetric dihydroxylation in the presence of an oxidant and a cinchona alkaloid compound in a solvent selected from the group consisting of water, acetone, acetonitrile and t-butanol, at a temperature in the range of −20 to 200° C. for a period ranging from 0.5 to 48 hrs and obtaining the desired chiral vicinal diol.

19. A process as claimed in claim 18 wherein the quantity of multifunctional catalyst used in the reaction is in the range of 0.01 to 10 mol % of active species with respect to the substrate.

20. A process as claimed in claim 18 wherein the multifunctional catalyst used is recovered by filtration and is reused for several cycles with consistent activity.

21. A process as claimed in claim 18 wherein the oxidant used is selected from the group consisting of N-methyl morpholine N-oxide (NMO), trimethylamine N-oxide, hydrogen peroxide, t-butyl hydrogen peroxide, potassium ferricyanide, sodium periodate and molecular oxygen.

22. A process as claimed in claim 18 wherein the cinchona alkaloid compound used is selected from the group consisting of $(DHQD)_2PHAL$, $(DHQD)_2PYR$, $(DHQD)_2AQN$, DHQD-OAc, DHQD-CLB, DHQD-PHN, DHQD-MEQ, DHQD-IND and other pseudoenantiomeric forms of such ligands.

23. A process for the preparation of a chiral vicinal diol from olefin using a reusable multifunctional catalyst having formula S—M, wherein S is a support selected from the group consisting of LDH, resin, silica, clay, alumina and S'—$NR_3X$ wherein S' is a unmodified support selected from resin and silica, R is an alkyl group selected from the group consisting of methyl, ethyl, propyl and butyl, X is selected from the group consisting of Cl, Br, I, F, OH and OAc; M is an active species comprising two different transition metals selected from the group consisting of ruthenium, osmium, tungsten, titanium, vanadium, chromium, manganese, iron, cobalt, nickel, copper, and molybdenum, said process comprising reacting dihydroxylating the olefin using the said catalyst via N-oxidation in the presence of an oxidant and a cinchona alkaloid compound in a solvent selected from the group consisting of water, acetone, acetonitrile and t-butanol, at a temperature in the range of −20 to 200° C. for a period ranging from 0.5 to 48 hrs and obtaining the desired chiral vicinal diol, and wherein the reusable multifunctional catalyst is selected from the group consisting of LDH-PdOs, resin-PdOs, $SiO_2$—PdOs, SGS-$(QN)_2$PHAL-PdOs, LDH-OsW, resin-OsW, $SiO_2$—OsW, SGS-$(QN)_2$PHAL-OsW, SGS-$(QN)_2$PHAL-OsTi, LDH-PdOsW, resin-PdOsW, $SiO_2$—PdOsW and SGS-$(QN)_2$PHAL-PdOsW.

24. A process as claimed in claim 23 wherein the quantity of multifunctional catalyst used in the reaction is in the range of 0.01 to 10 mol % of active species with respect to the substrate.

25. A process as claimed in claim 23 wherein the multifunctional catalyst used is recovered by filtration and is reused for several cycles with consistent activity.

26. A process as claimed in claim 23 wherein the oxidant used is selected from the group consisting of N-methyl morpholine N-oxide (NMO), trimethylamine N-oxide, hydrogen peroxide, t-butyl hydrogen peroxide, potassium ferricyanide, sodium periodate and molecular oxygen.

27. A process as claimed in claim 23 wherein the cinchona alkaloid compound used is selected from the group consisting of $(DHQD)_2PHAL$, $(DHQD)_2PYR$, $(DHQD)_2AQN$, DHQD-OAc, DHQD-CLB, DHQD-PHN, DHQD-MEQ, DHQD-IND and other pseudoenantiomeric forms of such ligands.

* * * * *